US008750594B2

(12) United States Patent
Kovarik et al.

(10) Patent No.: US 8,750,594 B2
(45) Date of Patent: Jun. 10, 2014

(54) SYSTEM AND METHOD FOR NON-DESTRUCTIVELY EXAMINING DEGRADATION OF AN INTERIOR OF A DEVICE

(71) Applicant: Florida Power & Light Company, Juno Beach, FL (US)

(72) Inventors: James J. Kovarik, Bartlett, IL (US); Brent D. Burns, Elgin, IL (US); Kevin J. Urness, Saint Charles, IL (US)

(73) Assignee: Florida Power and Light Company, Juno Beach, FL (US)

( * ) Notice: Subject to any disclaimer, the term of this patent is extended or adjusted under 35 U.S.C. 154(b) by 0 days.

(21) Appl. No.: 13/633,546

(22) Filed: Oct. 2, 2012

(65) Prior Publication Data

US 2013/0028377 A1 Jan. 31, 2013

Related U.S. Application Data

(63) Continuation-in-part of application No. 13/236,301, filed on Sep. 19, 2011, now Pat. No. 8,280,145, which is a continuation-in-part of application No. 12/928,765, filed on Dec. 17, 2010, now Pat. No. 8,023,722.

(51) Int. Cl.
*G06K 9/00* (2006.01)

(52) U.S. Cl.
USPC .......................................................... 382/141

(58) Field of Classification Search
USPC ....................... 382/132, 141–152; 378/58–59
See application file for complete search history.

(56) References Cited

U.S. PATENT DOCUMENTS 7,190,177 B2 * 3/2007 Zoughi et al. ................. 324/642
7,653,175 B2 * 1/2010 Gordon et al. .................. 378/57

* cited by examiner

*Primary Examiner* — Daniel Mariam
(74) *Attorney, Agent, or Firm* — Feldman Gale, P.A.; Richard Guerra

(57) ABSTRACT

A system and method for monitoring degradation of a device having a metal layer and a composite layer, such as a vehicle-mounted boom arm. The system can include a collar mounted on an outer surface of the device, a radiography device movably coupled to the collar, and a monitor. The radiography device can include a source of radiography signals positioned to direct radiography signals through at least a portion of the device and a detector to detect radiography signals that have passed through the device. The monitor can be connected to the detector to display an image of the device generated from the detected radiography signals. Anomalies in the device image can represent degradation in the device.

15 Claims, 4 Drawing Sheets

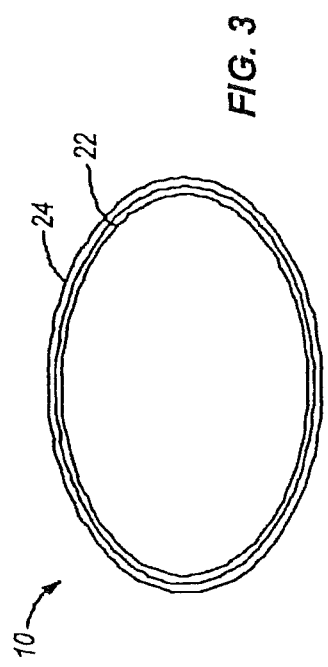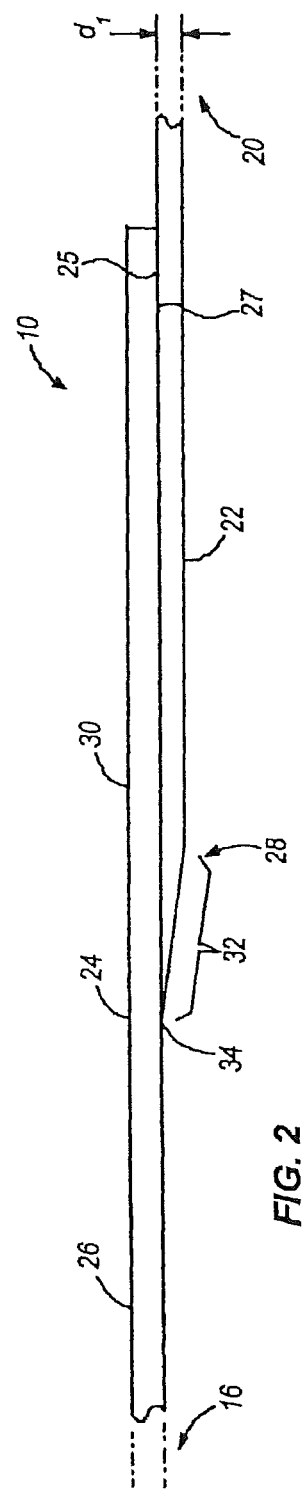

SYSTEM AND METHOD FOR NON-DESTRUCTIVELY EXAMINING DEGRADATION OF AN INTERIOR OF A DEVICE

RELATED APPLICATIONS

The present application is a continuation-in-part of U.S. application Ser. No. 13,236,301, filed Sep. 19, 2011 (U.S. Pat. No. 8,280,145), which is a continuation-in-part of U.S. patent application Ser. No. 12/928,765, filed Dec. 17, 2010 (U.S. Pat. No. 8,023,722), the entireties of which are incorporated herein by this reference.

FIELD OF THE INVENTION

The invention relates to a system and method for non-destructive examination of degradation, such as corrosion and wear, on a non-visible interior of a device having a metal layer bonded to a composite layer, such as a vehicle-mounted boom arm.

BACKGROUND

Telephone and utility service providers frequently inspect or repair lines, trees, and other objects located at elevated heights. Boom arms fitted with baskets are commonly mounted to vehicles for elevating personnel carried within the basket. Boom arms for such vehicles can be constructed in a variety of configurations, including, for example, an over-center boom arm that can unfold from a horizontal position to a vertical position.

Boom arms are typically hollow tubes that are strong and lightweight with a multi-layer construction. One type of boom arm has an inner metal layer bonded to an intermediate composite layer (e.g., a steel portion that extends 10 to 14 inches across a connection point between fiberglass portions). An outer layer is constructed of a protective material, such as a gel-coat, and is bonded or applied over the composite layer.

The metal layer and the composite layer have different stiffnesses. To provide a smooth transfer of bending stresses created by the load in the basket from the composite layer to the metal layer, the end of the metal layer is tapered over a region around the inner circumference of the boom arm. The tapered region allows a band of stress between the metal layer and the composite layer to dissipate. For example, the tapered region diffuses the stress into a band having a width of about six to ten inches. Without the tapered region, the stress would form a stress line, increasing the likelihood of failure of the composite layer.

The metal layer, and particularly the tapered region of the metal layer, is subject to degradation by, for example, corrosion or wear. When corrosion occurs, rust is produced and the thickness of the metal material at the tapered region is reduced. Because the production of rust does not occur uniformly, the remaining material at the tapered region forms into peaks and valleys, increasing the magnitude of stresses at stress points, rather than across a band. Rust is also worn into the composite layer adjacent to corrosion spots in the metal layer, eroding the composite material and reducing the strength of the composite layer. Finally, as metal and composite material at the tapered region is depleted by degradation, gaps form between the composite layer and the metal layer, reducing the generally uniform transfer of stresses at the tapered region.

Each vehicle-mounted boom arm can be subject to different environmental conditions depending on the use of the boom arm and the local climate. As a result, it is difficult to predict if and when degradation such as corrosion and wear will occur. Furthermore, because degradation occurs on the inside of the boom arm, there may not be any indicators of corrosion, erosion, wear etc. on the exterior or visible surface of the boom arm. In order to access the interior of the boom arm for examination, the boom arm would have to be disassembled or even destroyed with certain boom configurations.

SUMMARY

Accordingly, a need exists for a system and method of examining degradation, such as corrosion and wear, present on a non-visible interior of a device having a metal layer and a composite layer, such as a vehicle-mounted boom arm, without having to destroy or disassemble the device.

In one embodiment, the invention provides a method for non-destructively examining degradation on an interior of a device having a metal layer and a composite layer. Radiography signals are directed through a region of interest of the device, which includes the metal layer and the composite layer. Radiography signals that have passed through the device are detected. An image of the metal layer and the composite layer at the region of interest is generated from the detected radiography signals. Anomalies in the device image representing degradation in the region of interest are identified.

In another embodiment, the invention provides a system for non-destructively examining degradation on an interior of device having a metal layer and a composite layer. The system includes a collar sized and shaped to be mounted on an outer surface of the device, a radiography device movably coupled to the collar, and a monitor. The radiography device includes a source of radiography signals arranged to direct radiography signals through at least a portion of the metal layer and the composite layer and a detector for detecting the radiography signals. The monitor is connected to the detector to display an image of the device generated from the detected radiography signals.

In yet another embodiment, the invention provides a method for monitoring degradation on an interior of a device having a metal layer and a composite layer. A region of interest on an interior of the device is non-destructively examined for degradation, and the degradation is quantified. The device is placed in a first monitoring schedule if substantially no degradation is present on the device. The device is removed from service if a quantity of degradation in excess of a degradation threshold is present on the device. The device is placed in a second monitoring schedule if a quantity of degradation less than the degradation threshold is present on the device.

For the purposes of brevity while still complying with written description and enablement requirements, the following are hereby incorporated herein by this reference in their entireties to add further background and detail with respect to various cooling systems that can be inspected using various embodiments of the present invention: U.S. Pat. No. 7,082,774 to Nemoto, et al.; US20060266058 to Shiflet; US200690197053 to Shiflet; US20070019708 to Drost, et al.; US20050126211 to Narayanan; US20077171824 to Guerra, US20100328885 to Scofield.

Still other applications of the present invention include embodiments used in the area of cooling large concentrations of electronics, as found in telecommunications central offices, server rooms, military installations, etc., is becoming increasingly challenging. Space is often at a premium in these installations, and because of the continuous increase in the power dissipation of modern semiconductors, there is a need to greatly increase the volumetric cooling capacity, often expressed in Watts per liter. If cooling systems are unable to keep up with the expansion of volumetric thermal load, multiple problems are created, including overheated equipment, diminished system reliability, and human factor problems like fan noise and uncomfortably hot maintenance personnel.

Fluid cooling typically replaces at least some of the airflow with the flow of a fluid coolant or refrigerant that has much higher specific heat, and therefore much higher capacity to remove heat from the air surrounding dense electronics. For example, multiple coolant loops will be installed, where each loop receives cold coolant from a central device, such as a compressor, and distributes the coolant to cool specific loads. For example, evaporators may be used to cool frames or shelves, or fluid heat sinks to directly cool electronic components. Specialized control systems and coolant distribution apparatus are employed to manage the complexities of this new fluid cooling regime.

One problem with fluid cooling is that fluid cooling coils are typically fixed. Using fixed cooling equipment often makes access to the electronic equipment that is being cooled difficult. Therefore inspection of such systems is problematic.

Thus, in one embodiment, the present invention is directed to a method and system for non-destructively examining degradation of multiple coolant loops, wherein such multiple coolant loops have a metal layer and a composite insulation layer, the system comprising: a collar sized and shaped to be mounted on an outer surface of the multiple coolant loops; a radiography device movably coupled to the collar, the radiography device including a source of radiography signals positioned to direct radiography signals through at least a portion of the metal layer and the composite insulation layer and a detector to detect the radiography signals; and a computer connected to the detector to display graphical or numerical data of the multiple coolant loops generated from the detected radiography signals.

As illustrated in FIG. 5, certain embodiments of the present invention provide a collar mechanism that can accommodate a variety of diameters of the device being inspected. For example, FIG. 5 depicts a cylinder (in cross-section) around which a collar of the present invention can be fitted, with the collar preferably having at least one hinge and at least one latch so that the collar can be positioned around and connected to itself in a manner that enables the rotating elements (depicted on FIG. 5 as round circles with a diameter spanning cross-bar) to be positioned at various positions about the periphery of the cylinder.

One embodiment allows for the rotating elements (cams with a folcrum point) to be used solely for ease of attachment to a cylinder to be inspected. The collar would be opened sufficiently wide to allow placement of the cylinder to be tested to be located inside the collar. The latch on the collar would be secured, and then the manually adjustable or spring loaded cams will self center the cylinder to be inspected for proper orientation of the inspection device (radiographic, ultrasonic, or other methodology). The manually adjustable embodiment is envisioned to have a take up reel such that cables connected to the cams may be tightened so that the cams become engaged with the cylinder to be tested by friction. The take-up reel may also be pre-loaded prior to putting the collar on the cylinder to be tested so that when the collar is latched around the cylinder to be tested, spring tension in each of the cams is torqued by cables in the take-up reel, and the cables may be released so that the cams engage the cylinder by friction due to the spring tension in each of the cams. The cams are attached to the collar and may have varying diameters and lengths and can be made of various materials that will allow the greatest friction to the cylinder to be tested so that the inspection device does not move unintentionally in relation to the cylinder to be tested.

In another embodiment, the rotating elements have axles positioned in their centers. The rotating elements are used to "drive" the collar around the cylinder to be inspected while the inspection device is mounted to the collar. The axles of the rotating elements can be spring loaded so as to center the collar about the cylinder and maintain sufficient force to enable the collar to be manually manipulated around the cylinder, or the rotating elements may be motorized so that remote maneuvering of the collar and inspection device around the cylinder to be tested is possible.

In a third embodiment, the rotating elements of the collar are oriented perpendicularly to the axis of the cylinder to be tested and may be spring-loaded or otherwise adjustable by screw, cable or other mechanical means to contact the cylinder to be tested and the collar would then be "driven" axially along the cylinder to be tested with the inspection device mounted to the collar.

In a fourth embodiment, two or more sets of rotating elements are incorporated into the collar allowing for circumferential and/or axial motion of the collar along the cylinder to be tested while the inspection device is mounted to the collar. Motion may be manual or motorized.

As one of skill in the art will appreciate, the rotating elements can be operably associated with one or more sensors or x-ray transmitting devices so that inspection of the cylinder (e.g. a pipe, a refrigeration coil, an aircraft conduit, etc.) can be achieved. The rotation about the cylinder can be manually or automatically governed in a manner such that desired distances and speeds of travel of the scanning device is achieved, dependent upon the level of inspection required, the types of degradation at issue, the thickness and composition of various materials being scanned, etc. One will appreciate also that in addition to x-ray devices, other sensing units can be employed—such as ultra-sonic devices that are able to detect different types and kids of defects and/or that provide information as to the position of the scanning unit within a length of an over-all system being inspected. For example, GPS positioning can be employed and suitable units of GPS devices associated with the scanning device of the present invention (e.g. including associating such GPS devices as part of the collar) such that an operator thereof can determine precisely what portions of a cylinder have been examined, what features have been observed at defined positions along the cylinder, etc.

In a particular embodiment, (again referring to FIG. 5) there is preferably at least one hinge and an opposing latch such that the collar can be reversibly connected around a cylinder that is to be inspected. A series of pulleys are associated with the collar at radially spaced positions and a cable attachment is operatively associated with such pulleys so that an operator of the unit can adjust the positions of the rotating elements. The cable can be associated with a manual or spring operated/loaded take up reel. The pivot points for each of the rotating elements is depicted in FIG. 5, which are distinct in preferred embodiments to the cable attachment points. The hinge/latch embodiments of the present invention thus provide a simple way to facilitate the inspection of various sized cylinders—as well as to accommodate either slight or more severe changes in the diameter of a cylinder throughout its length (e.g. due to perhaps increased insulation between one section and another; or different composite materials being employed for various sections of an extended cylinder/pipe/conduit due to the different environmental conditions such sections may be exposed to, etc.) The latch mechanism can be of any type, including simple pivot mechanisms that will be known to those of skill in the art. Other more flexible attachment means can be employed, however, including wrap around Velcro bands (e.g. to form a collar with desired instrumentation associated therewith, including but not limited to GPS devices, x-ray inspection units, ultra-sonic units, etc.), such that it is possible to avoid rigid hinges and latches when the conditions for inspection are not adaptable for the use of such structures.

Other aspects of the invention will become apparent by consideration of the detailed description and accompanying drawings.

BRIEF DESCRIPTION OF THE DRAWINGS

FIG. 2 is a longitudinal cross-sectional view of a portion of a boom arm.

FIG. 3 is a lateral cross-sectional view of the boom arm of FIG. 2.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings, and can include electrical connections or couplings, whether direct or indirect.

It should be noted that while certain particular embodiments are directed to a boom arm, such description is intended to relate to one of skill in the art the many possible variations that are included within the scope of the present invention. The boom arm mentioned should thus be considered as a particular embodiment where the present system can be employed. It finds numerous other uses, in particular, in use with tubular goods. Tubular goods are used in a variety of industrial applications, which may be particularly sensitive to internal defects. For example, a particular tubular good may have internal-external thickness variations, hairline fractures, seams, and various other longitudinally-oriented, transversely-oriented, and obliquely-oriented defects, which may be undetectable by alternative inspection techniques. These defects may arise during the initial manufacturing process, the subsequent processing or transportation, or they may occur as service-induced defects. In many industrial applications, the foregoing defects may lead to environmental damage, bodily injury, equipment damage and downtime, and loss of the associated product, such as hydrocarbon reserves.

Figure 1:
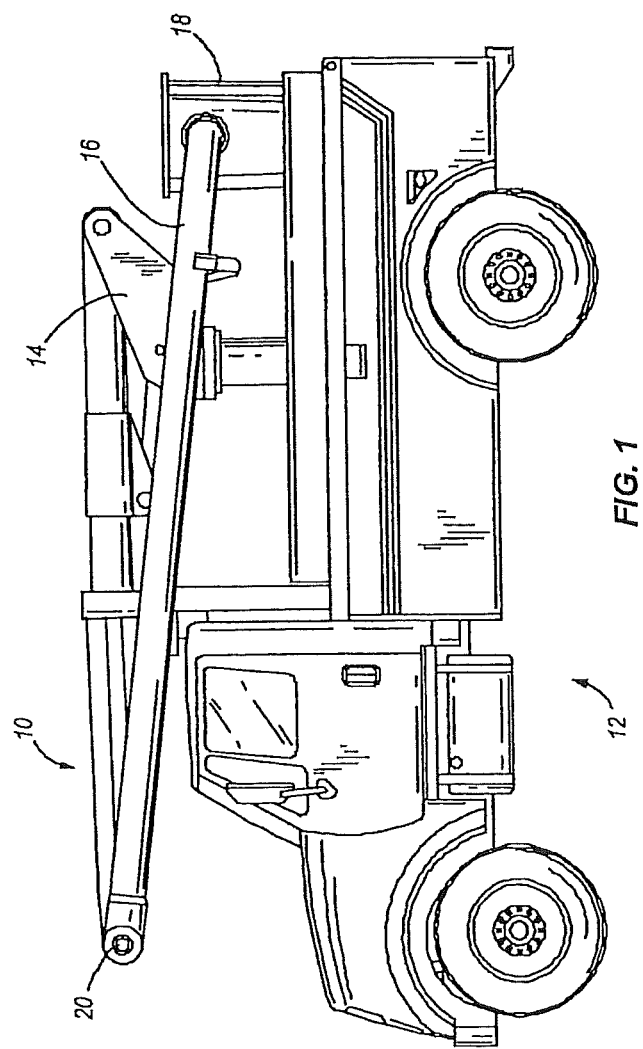
FIG. 1 is a side view of a motorized vehicle with a boom arm in a folded configuration.

FIG. 1 illustrates a boom arm 10 mounted to a motorized vehicle 12 of the type commonly used to access elevated objects, such as power lines and trees. A first end 14 of the boom arm 10 is mounted to the vehicle 12, while a second end 16 of the boom arm 12 is coupled to a passenger basket 18. The boom arm 10 can include an elbow joint 20 so that the boom arm 10 can be stored folded into a horizontal or lengthwise configuration while not in use, as shown in FIG. 1. The boom arm 10 can be unfolded into a vertical position with the basket 18 elevated while in use.

Figure 5:
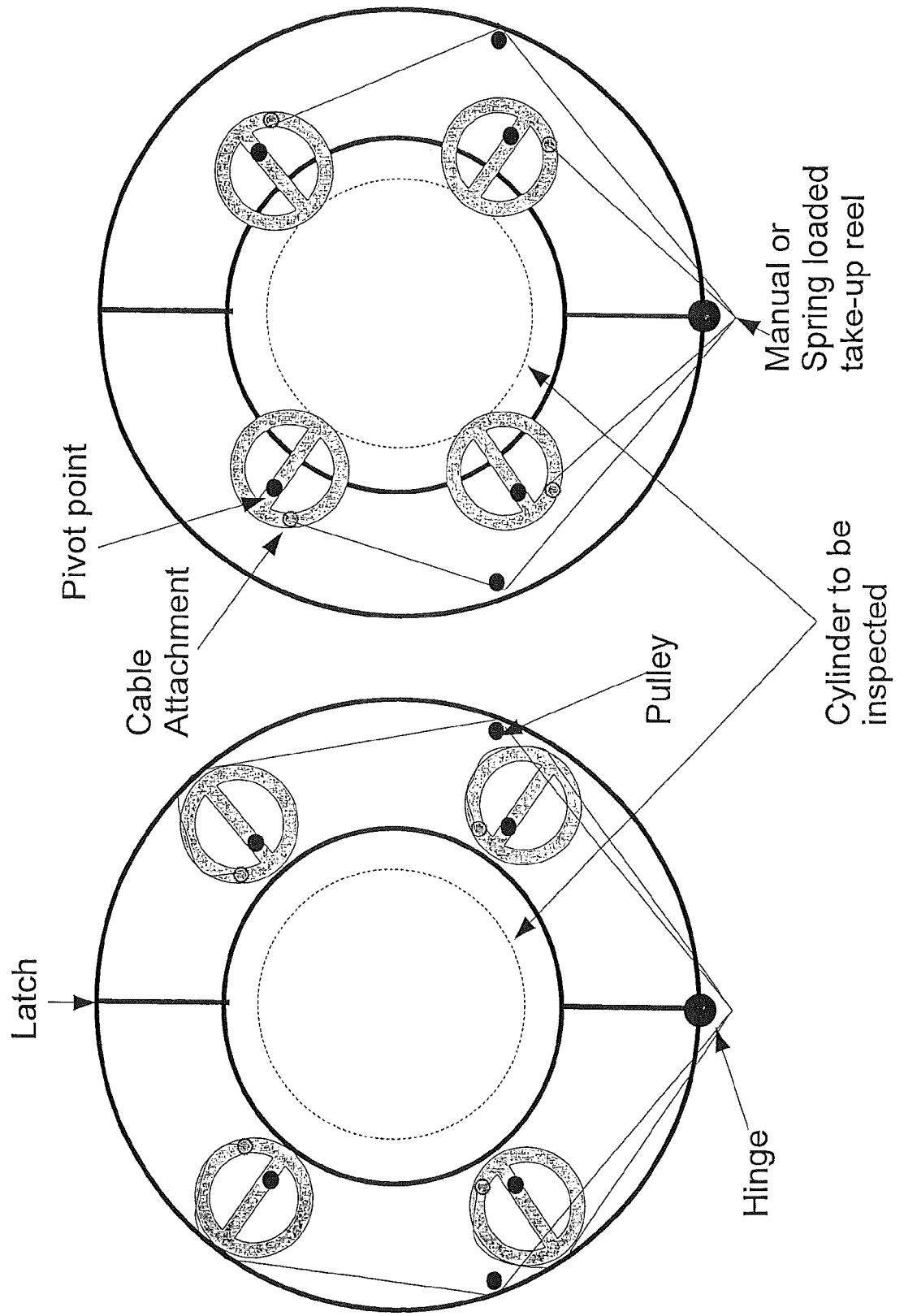
FIG. 5 illustrates one embodiment useful for the inspection of refrigeration system lines.

FIGS. 2 and 3 illustrate the construction of the boom arm 10, which is a multi-layer hollow, tubular member. This type of multi-layer construction may also be present in other types of devices or equipment, such as wire spreaders, cranes, platform lifts, cable placers, etc. In the electric utility industry specifically, composite materials are used primarily for construction in order to provide insulation from the electric line voltages. Metals are generally only used to reinforce the joints between composite structures. However, failure occurs at these metal-reinforced joints between composite structures. As shown in FIGS. 2 and 3 for a vehicle-mounted boom arm 10, an inner layer 22 of the boom arm 10 is generally formed of a metal, such as steel. An intermediate layer 24 of the boom arm 10 is generally formed of a composite material, such as fiberglass. An inner surface 25 of the composite layer 24 is bonded to an outer surface 27 of the metal layer 22 to secure the layers to one another. A tapered or transition region 32 is formed at an end 28 of the metal layer 22, where the metal layer 22 is tapered from a first thickness $d.sub.1$ to a pointed or almost pointed edge 34 extending around the circumference of the metal layer 22. However, the transition region 32 may not be tapered in some boom arms. The composite layer 24 is generally longer than the metal layer 22, so that an end 26 of the composite layer 24 forms a tube extending beyond the end 28 of the metal layer 22. As shown in FIG. 5, an outer layer 36, such as a gel coat, of the boom arm 10 can be a protective coating formed or bonded to the intermediate layer 24.

Figure 4:
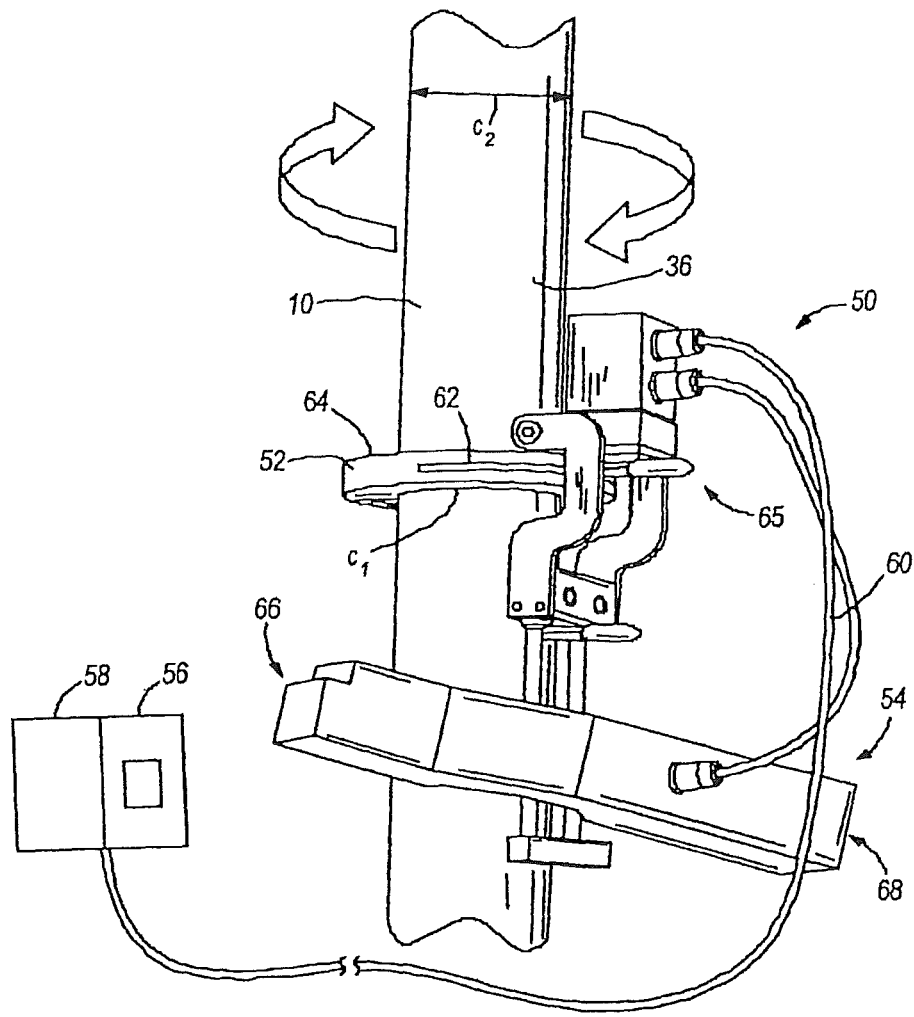
FIG. 4 is a perspective view of a radiography degradation detection system according to one embodiment of the invention mounted to a boom arm.

FIG. 4 illustrates a radiography degradation detection system 50 according to one embodiment of the invention mounted to boom arm 10. The detection system 50 can include a collar 52, a radiography device 54 coupled to the collar 52, and a monitor 56 connected to the radiography device 54.

The collar 52 can be a ring-like member sized and shaped for mounting to an outside of the boom arm 10. An inner circumference $c.sub.1$ of the collar 52 can be slightly greater than an outer circumference $c.sub.2$ of the boom arm 10. The collar 52 can include a hinge or other mechanism to facilitate at least partially opening and mounting the collar 52 to the boom arm 10. The collar 52 can include a securing mechanism 62 to secure the collar 52 to the boom arm 10. The securing mechanism 62 can be a clamp, a compression collar, a magnet, bolts, etc.

In some embodiments, the collar 52 can include a track 64 along which the radiography device 54 can move. The radiography device 54 can be coupled to the collar 52 and can be moved around the circumference of the boom arm 10 by moving along the track 64. The radiography device 54 can include a movement mechanism 65, such as a motor, for coupling the radiography device 54 to the collar 52 and for moving the radiography device 54 along the track 64. In one embodiment, the radiography device 54 can be moved about 360 degrees along the track 64 in order to move around substantially the entire circumference of the boom arm 10. In another embodiment, the radiography device 54 can be moved about 180 degrees along the track 64 or about half of the boom arm circumference.

As shown in FIG. 4, the radiography device 54 includes a source 66 of radiography signals 67 and a detector 68 for detecting radiography signals. In one embodiment, the radiography signals 67 are X-ray signals. The source 66 of radiography signals 67 and the detector 68 can be spaced apart on the collar 52 and can be positioned so that radiography signals 67 from the source 66 are directed into the boom arm 10 through both the metal layer 22 and the composite layer 24 toward the detector 68. The detector 68 can be positioned to detect radiography signals 67 which have passed through the boom arm 10. The degradation detection system 50 can be mounted to the boom arm 10 so that the radiography signals 67 pass through a region of interest of the boom arm 10, such as the tapered region 32.

As shown in FIG. 4, the monitor 56 can generate and display an image of the interior of the boom arm 10 from the radiography signals detected by the detector 68. The monitor 56 can be a handheld device, a personal computer, a laptop, or another suitable electronic device and can include a screen for displaying the image and/or data obtained from the detected radiography signals. The detected radiography signals can be displayed as still images or can be displayed as a moving image as the radiography device 54 travels around the boom arm 10 along the track 64. The monitor 56 can display substantially all or a portion of the circumference of the boom arm 10 at a given time. In one embodiment, the monitor 56 displays approximately an 11 degree arc of the boom arm 10 circumference at a given time. The degradation detection system 50 can include a control mechanism 58 that controls movement of the radiography device 54, as well as overall operation of the degradation detection system 50. The degradation detection system 50 can further include cables and connectors 60 for connecting the radiography device 54 to the monitor 56 and/or to other components of the degradation detection system 50. The cables and connectors 60 can be replaced with a wireless connection.

In one embodiment, visual analysis of the image of the boom arm 10 on the monitor 56 is used to identify and/or quantify degradation of the boom arm 10. This analysis can be performed manually by the operator of the degradation detection system 50 upon viewing the image on the monitor 56. In other embodiments, a software program, image analysis tool, or other computerized device can be used to automatically analyze the image of the boom arm 10 to identify and/or quantify degradation. In still other embodiments, a software program, signal analysis tool, or other computerized device can be used to analyze not the image, but the detected radiography signals themselves, in order to identify and/or quantify degradation. Such computerized devices can be installed on a handheld device, laptop, or personal computer that is connected to the monitor 56 and/or the radiography device 54, or can be integrated into the monitor 56. The results of the analysis by the computerized device can be displayed on the monitor 56 or another suitable display device. In addition, such data can be archived, uploaded to a database, transmitted to another party, etc. Finally, in some embodiments, even though identification and quantification of degradation can be carried out automatically by a computerized device, the images of the boom arm 10 can also be displayed on the monitor 56 for visual review by the operator of the degradation detection system 50.

Incorporated herein by this reference are various patents and patent publications that one of skill in the art will appreciate can be used in conjunction with the teaching and guidance provided herein to perform particular operations on various devices and in varying conditions. For the purposes of brevity while still complying with written description and enablement requirements, the following are hereby incorporated herein by this reference in their entireties: U.S. Pat. Nos. 6,647,801; 7,719,266; 7,719,266; 7,773,725; 7,826,088; 6,392,421; and U.S. patent publication Nos.: 20090199642; 20090301202; 20100017137; 20100052670; 20100106431; 20100107767; 20100199767; 20100207620; 20100236330; 20100278373; and also U.S. Pat. No: 7,190,177 to Zoughi; U.S. Pat. No. 7,937,229 to Buyukorturk, et al.; U.S. Pat. No. 8,014,586 to Sons, et al; U.S. Pat. No. 8,000,517 to Spitzer, et al; U.S. Pat. No. 7,933,441 to Numata, et. al.; U.S. Pat. No. 7,840,030 to Schmiegel, et al.; U.S. Pat. No. 7,989,729 to Zhao et al. and U.S. Pat. No. 7,916,929 to Maeda et al; and U.S. Pat. No. 4,586,379 to Burkhardt, Jr.

In some embodiments, the first detector may include a "bucket detector." A bucket detector refers to a multimode detector where all the modes propagating through an object are measured jointly. The bucket detector detects the presence, but not the location, of a photon. A bucket detector collects all the photons scattered by the object and acts like a time gate for a second detector. A time gate allows the second detector to know when to begin its observation and start counting coincidences.

In certain embodiments, a detector assembly and monitor which produces a real-time visible image may be supplanted with a detector employing a measurement device and display which produces a real-time display depicting density or material detected. In other embodiments, in addition to movement of the system about either the collar or around the device (e.g. boom), the detector assembly is moved along an axis parallel to the centerline of the device (e.g. boom). Real-time images on monitors of degradation or corrosion between a composite layer and metal layer (insulated piping) using a tangential scanning technique can be accomplished by having at least two collars and at least two separate monitors provided. Also included in various embodiments are attachment mechanisms that permit the variation of orientations to provide desired visibility around or about a particular device, such as a boom. For example, a tipping detector assembly may be employed to provide visibility to degradation artifacts not visible in 'perpendicular' tangent orientation—thus permitting angular adjustability to improve inspections. Still other embodiments comprise, in addition to producing images or measuring at location at the boundary of a metal layer and composite layer, the ability to move the system along an arc in a plane perpendicular to the centerline axis of the device (e.g. boom/pipe) while simultaneously allowing for movement along a collar associated with or around the device. More than one imaging device can be employed to achieve desired detection, such that in addition to an x-ray tube, other types of diction systems can be employed, such as an alternate energy source, e.g. a gamma energy emitting radioactive isotope. Yet other embodiments involve the use of an X-ray tube (source) and detector/measurement assembly that is not mounted to a common platform and that is not fixed in position with respect to each other. In certain embodiments a color is not employed at all, but rather is replaced with an external measurement system that determines the position of the source and the position of the detector and computes their position with respect to the other.

In various embodiments, the present system can be employed in a wide variety of fields, such as in the assessment of the integrity of insulated conduits, cables, pipelines and other interconnection systems for the purpose of understanding the location, degree and risk of damage and deterioration, and the probable causes thereof.

Structures that support transport of diverse electrical and electromagnetic signals, fluids, gases, and solids can be called "conduits". This application uses the term "conduit" for any structure supporting transport that can fail from accumulated damage or deterioration such as a cable, cable bundle, hydraulic or pneumatic hoses, pipes, or fuel lines. Conduits and conduit components deteriorate over time and are frequently damaged due to stress factors called "Stressors" including but not limited to abrasion, vibration, stresses, strains, chemicals, and heat) that exist both without and within conduits. If left undetected and allowed to take its course, the damage caused by stressors can cause damage of said components grounding, shorting, leaks of substances carried in the conduits. The damage can occur in moments or take an extended period of time. Often the failure happens unexpectedly, before a system's operator knows of the problem. In practice, conduits are usually encased by an insulating material and sometimes sheathed with one or more layers of cladding to assure continued functionality and safety. In certain situations it is important to know the degree of risk and status of health and integrity of conduits, contained conductors, and related components that comprise them. Conduits and systems of conduits may carry electrical power, fuel, other fluids, pneumatics, optical or electromagnetic signals. Deterioration and damage to cladding and insulation can be, and often is, a precursor to a failure in a system. Damages to interconnection systems includes, but are not limited to, chafing due to vibration, corrosion due to caustic chemicals, incisions, due to sharp edges, stress and strain due to motion, burning, oxidation, reduction and other chemical reactions, as well as chemical and physical degradation due to aging.

One aspect of the present invention is directed to aircraft wiring conduits, although the following statements have broad application in other uses for conduits of other types in other applications. In older fly-by-cable aircraft, chafed, cut electrical harnesses, control cables and hydraulic conduits used to control flight surfaces, landing gear, fuel supplies and engines have been known to cause loss of control of aircraft and fatal crashes.

Damage to aircraft conduits is known to cause catastrophic failure due to loss of signals to control systems, loss of hydraulic fluid, and other situations. Even when control systems remain intact, toxic fumes, and dense toxic smoke from smoldering or fire can make it impossible for a pilot to safely fly the aircraft. Intense heat from burning aromatic polyimide electrical wiring insulation and other combustibles can melt other insulation in seconds leading to collateral damage, more shorts and further loss of control.

Considering the extreme safety hazards of loss of control, toxic fumes, toxic smoke, fires or fuel tank explosions of aircraft it is not only important to know that deterioration or damage such chafing, arcing, or cut wires has occurred but also that a situation exists that likely will cause it to happen during flight. It would be very desirable therefore to have a system that could detect such deterioration for the purpose of detecting evidence of significant causes of deterioration, damage and failure of conduits as well as the degree of ongoing deterioration and damage. Use of the present system to detect such deterioration of conduits in aircraft is but one of many applications of the present inventions.

Another aspect of the present invention is directed to certain industrial tubes or piping and the inspection thereof to evaluate integrity thereof. For example, steam generator tubes of a nuclear power plant often undergo various kinds of corrosion and mechanical damage, such as stress corrosion cracking, pitting, inter-granular attack, wear, etc. Such corrosion and degradation are principal factors that affect the safety and integrity of major components of nuclear power plants. The occurrence of through-wall cracking of a steam generator tube may result in the serious contamination of a system and environment due to the leakage of primary coolant, including the radioactive contamination of a secondary side. One aspect of the present system is to facilitate location of through-wall cracking in an early stage and to measure its size and length accurately.

In certain embodiments, the present invention relates generally to the prevention of undesired releases or leaks of refrigerants, such as ammonia, in ammonia refrigeration systems, where the gaseous medium is toxic, or explosive, or both. More particularly, the system is employed to detect the onset of system conditions which are potentially dangerous to the integrity of a gaseous system, and detects such conditions before a rupture or other disaster to the system results. Cooling systems, and particularly commercial refrigeration systems, are predominantly pressurized gas driven, and ammonia is the current coolant of choice for such systems. However, free ammonia is considered toxic, and when used in a refrigeration system where expansion and compression of the gaseous medium is constantly taking place, the opportunity for breach of the system, with the concurrent escape of toxic gasses, is great. Depending on the gaseous medium, a rupture of the system could have calamitous results.

The beneficial effects of employing ammonia as a working refrigerant in vapor compression refrigeration systems has been known. Those skilled in the art have recognized that ammonia has many advantages when utilized as a refrigerant. As a first matter, it has a high critical temperature; and secondly, a low triple point temperature which allows it to be applied over a wide range of applications. Ammonia has a latent heat of vaporization which is considered high and which reduces the mass flow required for any given refrigeration load. The direct result of this latent heat of vaporization is that for a given refrigeration load, the resulting liquid line sizes are relatively small. Still further, other thermodynamic and thermophysical properties of ammonia result in good heat transfer coefficients. This results in efficient and compact heat exchanger designs being employed in various applications.

Ammonia is also considered to be an environmentally friendly, or "green" refrigerant since it occurs in nature and has no known capacity for depleting ozone in the atmosphere. It further has no apparent global warming potential. Those skilled in the art recognize that ammonia is used widely in a number of industry segments and in various applications Ammonia is relatively easy to produce and is low in cost as compared to other halo-carbon refrigerants now being employed.

While ammonia has been known for a long period of time and has many advantages, it also has some disadvantages which have detracted from its usefulness. Chief among its shortcomings is that ammonia is toxic in high concentrations; is an irritant in low concentrations; and further has a very pungent order when released. Still further, ammonia is flammable in a narrow range of concentrations with air. Another serious shortcoming with ammonia is that ammonia has a significant affinity for water. Ammonia readily reacts with any water which may inadvertently get introduced to a refrigeration system and thereafter holds the water tightly in solution. Thus, one aspect of the present invention is to provide a system and method that can detect water in such refrigeration units to prevent undesired consequences presented by the presence of water. It has been known that it is extremely difficult to keep water out of a prior art ammonia refrigeration system. Unfortunately, even in small amounts, an aqueous ammonia refrigerant can significantly increase the boiling point of the refrigerant mixture resulting in reduced refrigeration system performance, and increased operating costs. Typically, the presence of only a small amount of water in the prior art ammonia refrigeration system will typically cause an expansion valve control function to fail. If this failure is left unintended the ever increasing concentration of water in the refrigerant increases the boiling point of the ammonia-water concentration until the expansion valve controller is no longer able to sense the correct amount of superheat in any resulting refrigerant vapor. If left uncorrected, this same ammonia-water refrigerant can ultimately irreparably damage a compressor employed with the same refrigeration system.

Heretofore, industrial ammonia evaporators systems require relatively large inventories of liquid ammonia refrigerant circulating between various vessels and the evaporators employed with these systems. Direct expansion ammonia refrigeration systems have become quite attractive because they provide the ability to operate with a low ammonia refrigerant charge, which reduces the cost of manufacturing these same systems by allowing for the elimination of pressure vessels, pumps and the reduction of liquid line sizes. They also reduce the risks should an ammonia leak occur. The smaller amount of ammonia refrigerant being used is considered beneficial as it provides for lower insurance rates and further reduced EPA and OSHA health and safety requirements for installing and operating such systems.

OSHA regulation 29 CFR 1910.119 contains requirements for preventing or minimizing the consequences of catastrophic releases of toxic, reactive, flammable, or explosive chemicals. These releases may result in toxic, fire or explosion hazards and thus, one aspect of the present invention is to provide a system and method that can prevent unwanted releases of hazardous chemicals especially into locations which could expose employees and others to serious hazards. In one aspect of the present invention, the system is designed to particularly address issues arising in the ammonia refrigeration industry. For such an industry, as well as others similarly situated, an effective process safety management program requires a systematic approach to evaluating the whole process, but importantly, should include a system that can effectively detect points of corrosion in ammonia refrigeration systems. Wet insulation is one tell-tale sign of problems in this regard. Previously, there has not been a system or method that would non-destructively enable one to detect piping for suspected defects that leak or that are subject to leak such harmful vapors, gas, etc. Thus, use of the present system in the context of a process safety management policy implementation provides an aid to employers in their efforts to prevent or mitigate episodic chemical releases that could lead to a catastrophe in the workplace and possibly to the surrounding community. This can play a large role in developing a Mechanical Integrity and maintenance program that employs one or more of the present systems so as to minimize the risk of releases of undesired chemicals. The present system can be used as part of an incident investigation to facilitate employers learning from past experiences and thus avoiding repeating past mistakes so that the types of events which result in or could reasonably have resulted in a catastrophic release are identified and rectified.

In various aspects of the present invention, the following references, incorporated herein in their entireties by this reference, are relevant to provide written description and enablement for various embodiments. For example, these include: U.S. Pat. No. 7,661,574 to McGushion and U.S. Pat. No. 6,244,189 to Kingsley. Thus in one embodiment, the system includes a longitudinal track having a front for receiving a carriage and a back for mounting towards a work piece, a carriage adapted for holding a tool, a first wheel having a first axis, mounted on said carriage and disposed on the front of said track in contact with the front of said track for moving along said track, a second wheel having a second axis, connected to said carriage, disposed on the back of said track for moving along said track, and means for urging said second wheel toward said first wheel so that said second wheel applies radial force on the back of said track towards said first wheel. In a preferred embodiment, the collar of the present system is designed so that the collar, with associated x-ray detection instruments, can move along one axis, e.g. longitudinally, of the item being investigated, such a piping for a refrigeration system. The collar further provides the ability of the detection system employed to rotate around the piping when the collar is moved along such longitudinal aspect. Importantly, the system used with respect to ammonia refrigeration systems does not require that any of the insulation present on insulated piping be cut or otherwise physically affected so as to accomplish the inspection of such piping for water-logged areas, corrosion centers, etc.

Incorporated d by reference herein are relevant provisions of other regulations that provide guidance in understanding the aspects of the above referenced refrigeration art. For example, *Bulletin No.* 108. *Guidelines for Water Contamination in Ammonia Refrigeration Systems*. IIAR Ammonia Refrigeration Library, (1986). One aspect of the present invention is to provide a system that can locate sources of water, where it came from and to further address how to minimize continued infiltration. The present system thus provides an analytical and practical tool as to how one can discover and address water-type problems in an ammonia refrigeration system. Also incorporated herein by this reference is the *American National Standard for Equipment, Design & Installation of Ammonia Mechanical Refrigerating Systems*. IIAR Ammonia Refrigeration Library, (1999). The present system in one embodiment is employed to closed circuit mechanical refrigerating systems using ammonia as a refrigerant and provides one of the most efficient ways in which to address the ammonia leakage potential in such system using a system that non-destructively locates sources of concern in such ammonia mechanical refrigerating systems.

One embodiment of the present invention is directed to a system for non-destructively examining degradation on an interior of a device having a metal layer and a composite layer, where such system includes a collar sized and shaped to be mounted on an outer surface of the device and a radiography device movably coupled to the collar. The radiography device produces radiography signals that, when the device is properly positioned, are directed through at least a portion of the metal layer and the composite layer. A detector is then employed to detect the radiography signals. A computer connected to the detector is used to display graphical or numerical data relevant to the device that is generated from the detected radiography signals. In a preferred embodiment, the collar is a ring-like member sized and shaped for mounting to an outside of a cylinder, such as a pipe, a vessel, or a tank. In certain embodiments, the collar has an inner circumference that is slightly greater than an outer circumference of the device to which the collar is associated, such as a boom arm. In still other embodiments, the collar includes a hinge to facilitate at least partially opening and mounting the collar to the boom arm. It can also include a securing mechanism to secure the collar to the boom arm, such securing mechanism selected from the group consisting of a clamp, a compression collar, a magnet, and a bolt. In certain embodiments, the collar includes a track along which the radiography device can move, and in others, the radiography device is coupled to the collar in a manner so that it is movable 1) around the circumference of the device; 2) along the axis of the device; and 3) along a path perpendicular to the axis of the device. In particular it is preferable for the device to be movable about 360 degrees along the track in order to move around substantially the entire circumference of the device; movable along a path perpendicular to the axis of the device substantially encompassing an entire cross-section of the device; and movable along a path parallel to the axis of the device in order to move along substantially the length of the device. In other embodiments, there are more than one source of radiography signals and more than one detector is spaced apart on the collar.

Thus, the invention provides, among other things, a system and method for non-destructive examination of degradation on an interior of a boom arm. Various features and advantages of the invention are set forth in the following claims.

What is claimed is:

1. A system for non-destructively examining degradation of an ammonia refrigeration line, wherein such line has a metal layer and a composite insulation layer, the system comprising: a collar sized and shaped to be mounted on an outer surface of the ammonia refrigeration line; a radiography device movably coupled to the collar, the radiography device including a source of radiography signals positioned to direct radiography signals through at least a portion of the metal layer and the composite insulation layer and a detector to detect the radiography signals; and a computer connected to the detector to display graphical or numerical data of the ammonia refrigeration line generated from the detected radiography signals, wherein the radiography device is coupled to the collar in a manner so that it is movable about at least one of: 1) around the circumference of the ammonia refrigeration line; 2) along the axis of the ammonia refrigeration line; and 3) along a path perpendicular to the axis of the ammonia refrigeration line.

2. The system as set forth in claim 1, wherein the collar is a ring-like member sized and shaped for mounting to an outside of a cylinder.

3. The system as set forth in claim 2, wherein the collar has an inner circumference is slightly greater than an outer circumference of the ammonia refrigeration line.

4. The system as set forth in claim 2, wherein the collar includes a hinge to facilitate at least partially opening and mounting the collar to the ammonia refrigeration line.

5. The system as set forth in claim 2, wherein the collar includes a securing mechanism to secure the collar to the ammonia refrigeration line, said securing mechanism selected from the group consisting of a clamp, a compression collar, a magnet, and a bolt.

6. The system as set forth in claim 2, wherein the radiography device is 1) movable about 360 degrees along the track in order to move around substantially the entire circumference of the ; 2) movable along a path perpendicular to the axis of the ammonia refrigeration line substantially encompassing an entire cross-section of the ammonia refrigeration line; and, 3) movable along a path parallel to the axis of the ammonia refrigeration line in order to move along substantially the length of the ammonia refrigeration line.

7. The system as set forth in claim 2, wherein a source of radiography signals and a detector are spaced apart on the collar.

8. The system as set forth in claim 1, wherein the collar includes a track along which the radiography device can move.

9. A system for non-destructively examining degradation on an interior of an aircraft conduit that has a metal layer and a composite layer, the system comprising: a collar sized and shaped to be mounted on an outer surface of the aircraft conduit; a radiography device movably coupled to the collar, the radiography device including a source of radiography signals positioned to direct radiography signals through at least a portion of the metal layer and the composite layer and a detector to detect the radiography signals; and a computer connected to the detector to display graphical or numerical data of the aircraft conduit generated from the detected radiography signals, wherein the radiography device is coupled to the collar in a manner so that it is movable about at least one of: 1) around the circumference of the aircraft conduit; 2) along the axis of the aircraft conduit; and 3) along a path perpendicular to the axis of the aircraft conduit.

10. The system as set forth in claim 9, wherein the collar is a ring-like member sized and shaped for mounting to an outside of an aircraft conduit.

11. The system as set forth in claim 9, wherein the collar has an inner circumference is slightly greater than an outer circumference of the aircraft conduit.

12. The system as set forth in claim 9, wherein the collar includes a hinge to facilitate at least partially opening and mounting the collar to the aircraft conduit.

13. The system as set forth in claim 9, wherein the collar includes a securing mechanism to secure the collar to the aircraft conduit, said securing mechanism selected from the group consisting of a clamp, a compression collar, a magnet, and a bolt.

14. The system as set forth in claim 9, wherein the radiography device is coupled to the collar in a manner so that it is movable 1) around the circumference of the device; 2) along the axis of the aircraft conduit; and 3) along a path perpendicular to the axis of the aircraft conduit.

15. The system as set forth in claim 9, wherein a source of radiography signals and a detector are spaced apart on the collar.

* * * * *